United States Patent [19]

Wulff et al.

[11] 4,278,760
[45] Jul. 14, 1981

[54] METHOD AND COMPOSITION FOR DETERMINING AN OXIDIZED PYRIDINE CO-ENZYME

[75] Inventors: Karl Wulff, Weilheim; Fritz Stähler; Gerhard Michal, both of Tutzing, all of Fed. Rep. of Germany

[73] Assignee: Boehringer Mannheim GmbH, Mannheim-Waldhof, Fed. Rep. of Germany

[21] Appl. No.: 58,873

[22] Filed: Jul. 19, 1979

[30] Foreign Application Priority Data

Aug. 1, 1978 [DE] Fed. Rep. of Germany ....... 2833723

[51] Int. Cl.³ .............................................. C12Q 1/66
[52] U.S. Cl. ........................................ 435/8; 435/26
[58] Field of Search ............................. 435/8, 25, 26

[56] References Cited

U.S. PATENT DOCUMENTS

| | | | |
|---|---|---|---|
| 3,331,752 | 7/1967 | Struck | 435/26 |
| 3,660,240 | 5/1972 | Chappelle et al. | 435/8 |
| 3,941,659 | 3/1976 | Koch et al. | 435/26 |
| 3,953,295 | 4/1976 | Monte et al. | 435/25 X |
| 4,097,338 | 6/1978 | Konttinen et al. | 435/26 |
| 4,202,938 | 5/1980 | Haeckel et al. | 435/26 X |
| 4,218,536 | 8/1980 | Maurukas | 435/26 X |
| 4,229,527 | 10/1980 | Ziegenhorn et al. | 435/26 X |
| 4,229,529 | 10/1980 | Michal et al. | 435/26 |

*Primary Examiner*—Thomas G. Wyse
*Attorney, Agent, or Firm*—Sprung, Felfe, Horn, Lynch & Kramer

[57] ABSTRACT

A method for the quantitative determination of an oxidized pyridine co-enzyme which comprises reacting a sample containing oxidized pyridine co-enzyme in the presence of its specific alcohol dehydrogenase with an aliphatic alcohol of 8 to 16 carbon atoms, oxidizing the aldehyde formed with reduced flavine mononucleotide and oxygen in the presence of luciferase and of the particular FMN-reductase which is independent of the co-enzyme to be determined and of the reduced substrate co-enzyme of the latter, and measuring the resulting light emission as a measure of the initial oxidized pyridine co-enzyme content.

14 Claims, 4 Drawing Figures

METHOD AND COMPOSITION FOR DETERMINING AN OXIDIZED PYRIDINE CO-ENZYME

This invention relates to a method and reagent for the direct determination of an oxidized pyridine co-enzyme. More specifically, the invention is concerned with such a method and composition using a bacterial bioluminescent system.

The oxidized pyridine co-enzyme is to be understood to be nicotinamide-adenine-dinucleotide (NAD) and nicotinamide-adenosine-dinucleotide phosphate (NADP).

The bacterial bioluminescent system consists of two enzymes, namely, a luciferase and a flavine-monoculeotide-reductase (FMN-reductase). This system occurs in photobacteria, for example, *Photobacterium fischeri, Photobacterium phosphoreum* and *Beneckea harveyi,* and catalyses the following reactions:

(1) $FMN + NAD(P)H \xrightleftharpoons{\text{FMN-reductase}} FMNH_2 + NAD(P)$ (2) $FMNH_2 + O_2 + \text{aldehyde} \xrightarrow{\text{luciferase}} FMN + \text{acid} + \text{light (495 nm)}$ NAD(P) here indicates an oxidized pyridine co-enzyme and NAD(P)H a reduced pyridine co-enzyme.

The intensity of the light emitted by this reaction is defined as a velocity:

$$I = \frac{d(hxv)}{dt}$$

and, depending upon whether the reaction is allowed to proceed as a first or pseudo-first order reaction with regard to $FMNH_2$ or to the aldehyde, the light intensity is proportional to the concentration of the $FMNH_2$ or of the aldehyde.

The bacterial luminescent system contains three different FMN-reductases, one of which is exclusively NADH-dependent, a second of which is exclusively NADPH-dependent and the third of which is not only NADH- but also NADPH-dependent.

It is already known to use the bacterial bioluminescent system, usually in the form of a crude preparation which contains a mixture of the FMN-reductases and luciferase, for the quantitative determination of the reduced pyridine co-enzymes, i.e. NADH or NADPH. If the system is saturated with aldehyde and FMN, then, with regard to the pyridine co-enzyme, the total reaction proceeds almost according to the pseudo-first order, i.e. the light intensity is proportional to the concentration of reduced pyridine co-enzyme. An advantage of this method is its extraordinarily high sensitivity which enables the reduced pyridine co-enzyme still to be determined exactly in concentrations of $10^{-12}$ to $10^{-13}$ mol/l. According to this known process, the oxidized pyridine co-enzymes can also, in principle, admittedly be determined but only when these have previously been completely converted into the reduced pyridine co-enzymes. This represents a considerable disadvantage, which is explained in the following:

The determination of the oxidised pyridine co-enzymes is of considerable importance in biochemical investigations. However, the determination of oxidized pyridine co-enzymes formed as intermediates in the course of previous reactions catalysed by dehydrogenases is of especial importance. Typical examples of this include the reactions catalysed by lactate-dehydrogenase, malate dehydrogenase and glutamate-dehydrogenase, which are illustrated by the following equations:

(3) $\text{pyruvate} + NADH \xrightleftharpoons{\text{LDH}} \text{lactate} + NAD$ (4) $\alpha\text{-ketoglutarate} + NAD(P)H + NH_3 \xrightleftharpoons{\text{Glu-DH}} L\text{-Glu} + NAD(P)$ (5) $\text{oxaloacetate} + NADH \xrightleftharpoons{\text{MDH}} \text{malate} + NAD$ These reactions are used to a large extent for the determination of pyruvate, α-ketoglutarate and oxaloacetate, especially in clinical analysis. Hitherto, two ways were known for measuring these reactions with the use of the bacterial bioluminescent system via the determination of the oxidized pyridine co-enzyme formed:

1. The preceding dehydrogenase reaction is allowed to proceed to completion, excess reduced pyridine co-enzyme is completely destroyed chemically, the more stable oxidized pyridine co-enzyme formed by the dehydrogenase reaction thereby remaining intact, whereafter the latter is converted into the reduced form and then measured with the bacterial bioluminescent system (see, for example, Analyt. Biochem., 78, 229–234). However, this process is very laborious and does not permit the continuous monitoring of a dehydrogenase reaction which proceeds with the formation of the oxidized pyridine co-enzymes.

2. An NAD(P)H-consuming and NAD(P)-producing reaction can, in principle, also be monitored via a continuous or discontinuous measurement of the NAD(P)H consumption. However, because of the enzyme-kinetic parameters of most of the dehydrogenase reactions, it would here be necessary to use such a high initial concentration of NADH or NADPH that, from the point of view of the assay technique, the light signal, corresponding to this concentration, generated by the bioluminescent system could no longer be converted in the highly sensitive instruments conventionally used for such measurements. Furthermore, the signal decrease to be expected, in comparison with the level of the initial signal, is so small that it can no longer be measured in instruments of comparatively low sensitivity. If a correspondingly low co-enzyme concentration is used, which can still be used for the measurement techniques, then the dehydrogenase reaction to be measured does not proceed optimally, a dependable measurement value is not obtained and, furthermore, there is the technical measurement problem that, starting from a very high initial light emission, a comparatively small signal decrease is measured.

Therefore, it is an object of the present invention to overcome these disadvantages and to find a direct way in which, in a coupled enzymatic reaction, a light signal is generated over a dark background which corresponds to, for example is proportional to, the concentration of the oxidized pyridine co-enzyme.

Thus, according to the present invention, there is provided a process for the quantitative assay for an oxidized pyridine co-enzyme with oxidation by oxygen in the presence of the luciferase system and measurement of the emitted light, wherein an oxidized pyridine co-enzyme is reacted in the presence of its specific alcohol dehydrogenase with an aliphatic alcohol containing 8 to 16 carbon atoms and the aldehyde formed is oxidized with reduced flavine-mononucleotide (FMNH$_2$) and oxygen in the presence of luciferase and of the FMN reductase which should not react with the co-enzyme to be determined, as well as of the reduced substrate co-enzyme of the latter, with light emission.

The principle of the process of the present invention consists in that the higher-chained aldehyde reacted in the luciferase-catalysed reaction is formed with the use of an alcohol-dehydrogenase from the corresponding alcohol, with reduction of the oxidized pyridine co-enzyme. In this way, it is possible to form the aldehyde in a concentration corresponding to the concentration of the oxidized pyridine co-enzyme which, in turn, brings about a light signal proportional thereto.

As already mentioned above, the process according to the present invention can be used for the determination of a pyridine co-enzyme which is already oxidized, i.e. NAD or NADP. However, it is also possible to carry out this determination solely within the scope of a previous dehydrogenase reaction, in the course of which the oxidized pyridine co-enzyme is first formed, and, in this way, to measure a substrate or enzyme of the preceding reaction. In the case of the first of these embodiments, it is possible to work with relatively crude enzyme preparations of the bacterial bioluminescent system, for example, crude or only slightly purified extracts of appropriate photobacteria. These crude preparations contain the luciferase and the FMN reductase in a concentration and with an activity which is sufficient for the process. If, on the other hand, the second embodiment of the process of the present invention is to be carried out, i.e. the determination of an oxidized pyridine co-enzyme which is formed in situ in the course of a preceding dehydrogenase reaction, then a purified FMN-reductase must be employed, i.e. one which is independent of the oxidized pyridine co-enzyme to be determined and does not contain any FMN-reductase activity which is dependent upon the oxidised pyridine co-enzyme to be determined.

Furthermore, depending upon which of the two oxidized pyridine co-enzymes is to be determined, there is used the particular specific alcohol dehydrogenase (ADH) which is dependent upon this co-enzyme. Thus, if NAd is to be determined, then there is used the ADH (EC 1.1.1.1) which can be obtained, for example, from equine liver or yeast. If NADP is to be determined, then there is used the NADP-dependent alcohol dehydrogenase (EC 1.1.1.2) which can be obtained, for example, from *Leuconostoc mesenteroides*. Since these enzymes are known, a more detailed description thereof is here unnecessary. The reactions catalyzed by these two types of alcohol dehydrogenases are illustrated in the following equations (6) and (7):

(6) NAD + alcohol 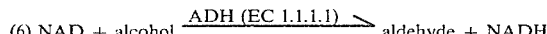 aldehyde + NADH (7) NADP + alcohol 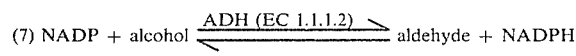 aldehyde + NADPH From Biochemistry, 12, 4911–4918/1973, it is already known that ADH from equine liver converts n-decanol to n-decanal and that the latter can be reacted with luciferase. However, it cannot be deduced from this that it would be possible to achieve a light emission which is directly dependent upon the NAD concentration in such a manner that a quantitative measurement is possible.

Depending upon whether the oxidized pyridine co-enzyme to be determined is NAD or NADP, there are thus the following courses of reaction, illustrated by the use of decanol:

NAD:

(8) decanol + NAD 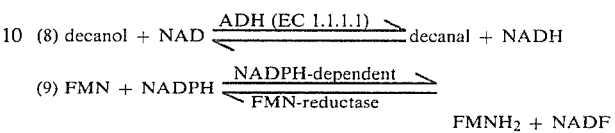 decanal + NADH (9) FMN + NADPH 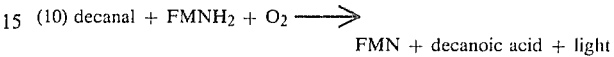 FMNH$_2$ + NADP

(10) decanal + FMNH$_2$ + O$_2$ ⟶ FMN + decanoic acid + light

NADP:

(11) decanol + NADP 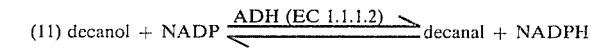 decanal + NADPH

(12) FMN + NADH 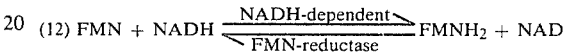 FMNH$_2$ + NAD

(13) decanal + FMNH$_2$ + O$_2$ ⟶ FMN + decanoic acid + light

When using a crude FMN-reductase preparation, which usually contains all three FMN-reductases, the specificity is achieved by the use of the appropriate reduced pyridine co-enzyme, i.e. in the case of NAD, this is NADPH and, in the case of NADP, this is NADH, so that interference due to reactions (9) or (12), respectively, can be avoided.

In the case of the second embodiment of the process according to the present invention, i.e. with a preceding dehydrogenase reaction, it is, however, necessary to introduce into the preceding reaction reduced pyridine co-enzyme formed in reactions (8) and (11), respectively, which is illustrated by the following equation:

(14) substrate + NAD(P)H 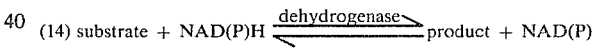 product + NAD(P)

It will be appreciated that the danger now exists that oxidized pyridine co-enzyme formed by reaction (9) or (12), respectively, will have a disturbing effect and that the equilibrium of reaction (8) or (11), respectively, can be disturbed when all three FMN-reductases can here exert their effectiveness. Therefore, in this case, an FMN-reductase preparation is employed which only has an activity for one of the two pyridine co-enzymes.

The process according to the present invention is carried out in buffered solution, pH values of from 6 to 9 generally being suitable. The choice of the pH value depends upon the particular enzymes used.

In the case of the alcohols used in the process, the lower members can be used as aqueous solutions but the higher ones have such a low solubility that they are used in the form of suspensions, which can be obtained, for example, by ultrasonic treatment. Surface-active materials are then preferably also added in order to stabilise these suspensions. Preferred surface-active agents include the non-ionic ones and especially the alkaryl-polyoxyethylene esters and ethers. This applies especially to tradecanol and hexadecanol but dodecanol can also be used in the form of a suspension.

The amount of alcohol to be used in the test, referred to ml. of test solution, is from 0.1 to 25 mMole/l. In the case of crude luciferase/FMN-reductase preparations, the corresponding amounts are from 0.5 to 50 μg. If purified enzymes are employed, then the activity amounts used correspond to these weight amounts. In the case of ADH, the introduced activities depend considerably upon the source of the enzyme and are generally from 0.05 to 300 mU. The particular reduced pyridine co-enzyme is preferably added in an amount of from 1 to $250 \times 10^{-6}$ Mole/l.

Furthermore, it can be desirable to add an organic SH compound, an amount of from 0.002 to 0.5 mMole/l here being preferred.

Finally, the buffer concentration to be used is preferably from about 2 to 130 mMole/l.

The present invention also provides a reagent for determining an oxidized pyridine co-enzyme, which comprises luciferase, FMN-reductase, an aliphatic alcohol containing 8 to 16 carbon atoms, a reduced co-enzyme, an alcohol dehydrogenase specific for the co-enzyme to be determined, flavine-monoculeotide (FNM), buffer and optionally an organic sulphhydryl compound and/or a surface-active agent.

According to a preferred embodiment, this reagent comprises:
0.5 to 50 μg/ml luciferase/FMN-reductase preparation
0.5 to 300 mU/ml alcohol dehydrogenase
0.01 to 25 mMole/l aliphatic alcohol containing 8 to 16 carbon atoms.
2 to 130 mMole/l buffer, pH 6 to 9 1 to $250 \times 10^{-6}$ Mole/l reduced co-enzyme
and optionally
0.002 to 0.5 mMole/l organic sulphhydryl compound/ml. test volume.

An especially preferred reagent composition comprises:
1.8 to 40 μg/ml luciferase/FMN-reductase preparation
1.3 to 2.7 mU/ml alcohol dehydrogenase
0.1 to 10 mMole/l alcohol
5 to 50 mMole/l buffer
5 to $150 \times 10^{-6}$ Mole/l reduced prydine co-enzyme
and optionally
0.005 to 0.5 mMole/l organic sulphhydryl compound/ml. test volume.

The SH compound used is preferably mercaptoethanol but other organic SH compounds, for example dithiothreitol, dithioertythritol, reduced glutathione or NAC (N-acetylcysteine), can also be used.

For a better understanding of the present invention, reference will be made to the accompanying drawing, in conjunction with the Examples. In the drawings.

The present invention provides, for the first time, an extremely sensitive and exact process for the measurement of an oxidized pyridine co-enzyme, with the help of the bacterial luminescent system, which can be carried out quickly and simply, can also be used together with preceding dehydrogenase reactions and can also be carried out with relatively simple and not especially highly sensitive measurement devices.

The following Examples further illustrate this. In these Examples, all light measurements were carried out with the use of the ATP photometer, Model 3000 of the firm SAI Technology Co., San Diego, Calif., U.S.A. The buffer used in each case was potassium phosphate buffer. However, other buffers which can be used include TRIS-acetate, triethanolamine hydrochloride and imidazole acetate, as well as TRIS-sulphate.

EXAMPLE 1

Determination of NAD concentrations with equine liver ADH (ED 1.1.1.1)

Reaction conditions: volume 2.0 ml.
end concentration in the test:
  80 mMole/l potassium phosphate buffer, pH−7.0
  0.1 mMole/l mercaptoethanol
  2.5 μMole/l FMN
  8 mMole/l decanol
  34 μg/ml luciferase/FMN-reductase (crude fraction from *Photobacterium fischeri*)
  5.4 mU/ml alcohol dehydrogenase from equinine liver (specific activity e.g. 2.7 U/mg.)
  $10^{-4}$ Mole/l NADPH
  $10^{-4}$ to $10^{-7}$ Mole/l NAD The reagents are mixed together, except for the pyridine co-enzymes. The reaction is then pre-started with NAD and, exactly 15 seconds after the NAD addition, started with NADPH. The light intensity gradually increases, the maximum light intensity being achieved after 3 to 5 minutes. The maximum intensity is the measurement value. The assay can also be carried out by starting simultaneously with a mixture of the two pyridine co-enzymes, NAD and NADPH.

Figure 1:
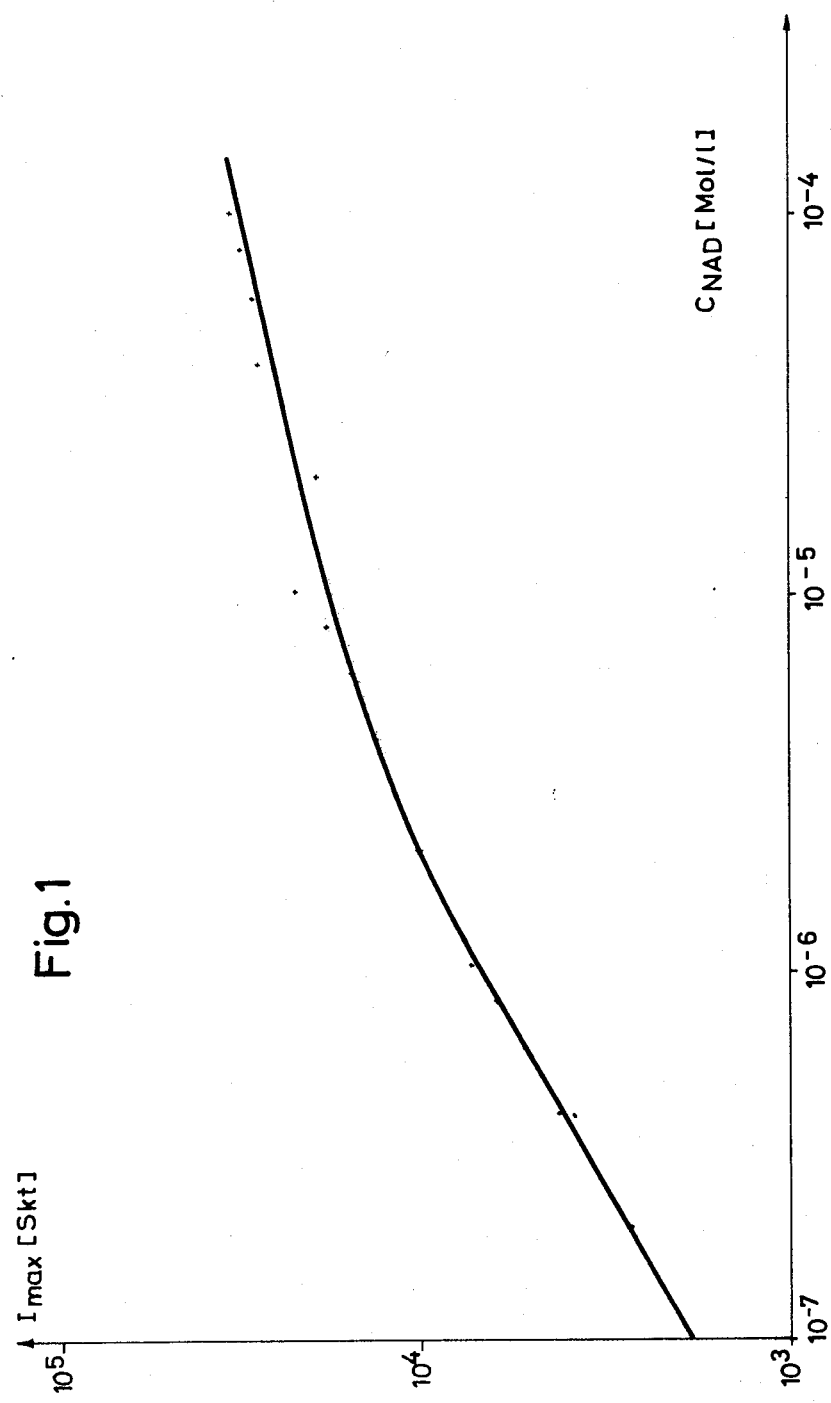
FIG. 1 is a graphic illustration of the relationship between the maximum light intensity and the NAD concentration in the case of the process of Example 1.

FIG. 1 illustrates the relationship between the maximum light intensity and the NAD concentration. Control values without NAD were also measured and, in each case, the light intensity thereof was subtracted from the measurement value.

EXAMPLE 2

Measurement of NAD concentrations with yeast ADH and decanol

The reaction conditions used are, if not otherwise stated, the same as in Example 1.

Instead of equinine liver ADH, there were used 0.18U/test of ADH from yeast with a specific activity of, for example, 300 U/mg.

Figure 2:
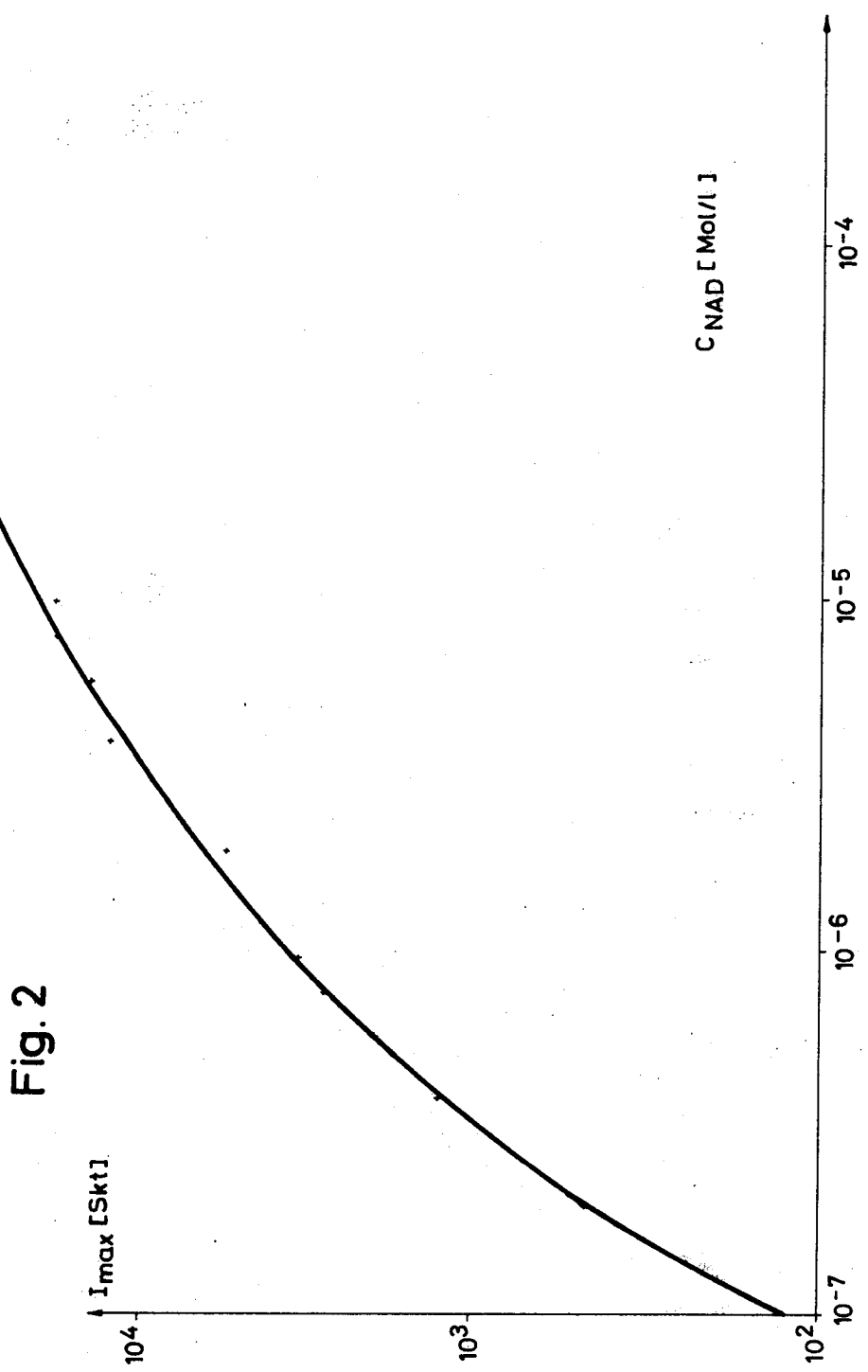
FIG. 2 is a graphic illustration of the relationship between the maximum light intensity and the NAD concentration according to Example 2.

The experimental results obtained are illustrated in FIG. 2. Variation range for the yeast ADH concentration: 0.05 to 18 U.

EXAMPLE 3

Determination of NAD concentrations in the presence of ADH from yeast or equinine liver with the use of higher chained alcohols, for example dodecanol and tetradecanol.

Figure 3:
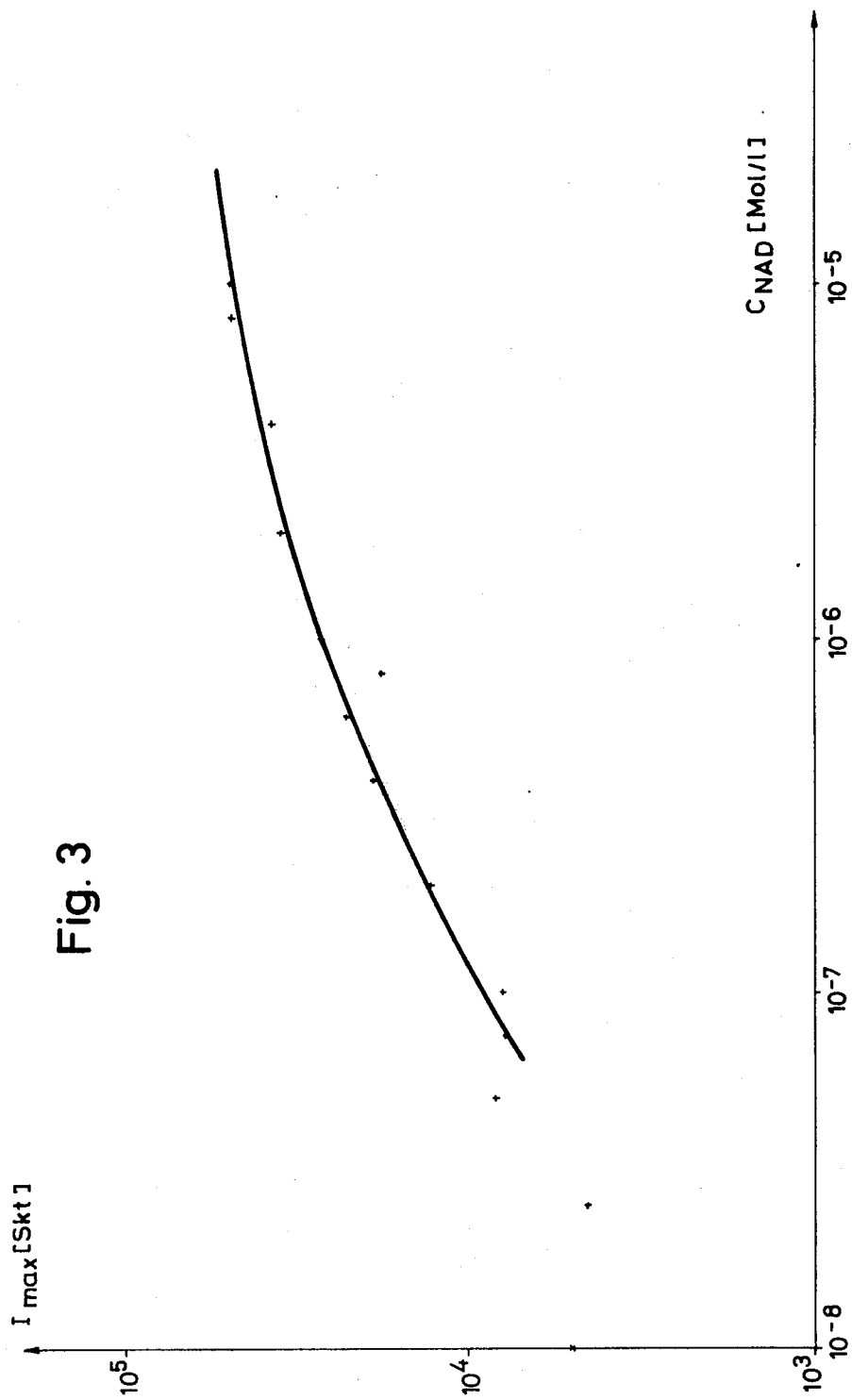
FIG. 3 is a graphic illustration corresponding to FIGS. 1 and 2, using a longer chained alcohol according to Example 3.

The reaction conditions used are the same as in Examples 1 and 2. However, instead of a decanol solution, use was made of ultrasonic suspensions of dodecanol or tetradecanol. The stock solutions were 0,4 Mole/l in water+0.1% "Triton" X-100. 20 μl. of this suspension were used in the test. The end concentration in the test is thus 4 mMole/l of dodecanol or tetradecanol. FIG. 3 shows the results obtained with tetradecanol and equine liver ADH.

EXAMPLE 4

Determination of NADP concentrations with the ADH from *Leuconostoc mesenteroides* (EC 1.1.1.2)

The experiment was carried out as described in Examples 1 to 3, except that NADH was used instead of NADPH.
Concentration: $10^{-5}$ Mole/l
Limits: $10^{-6}$ to $10^{-4}$ Mole/l.
NADP was determined in the concentration range of $10^{-7}$ to $10^{-4}$ Mole/l.
ADH from *Leuconostoc mesenteroides*;
Concentration: 6U/test
Limits: 0.1U to 30U/test.

Figure 4:
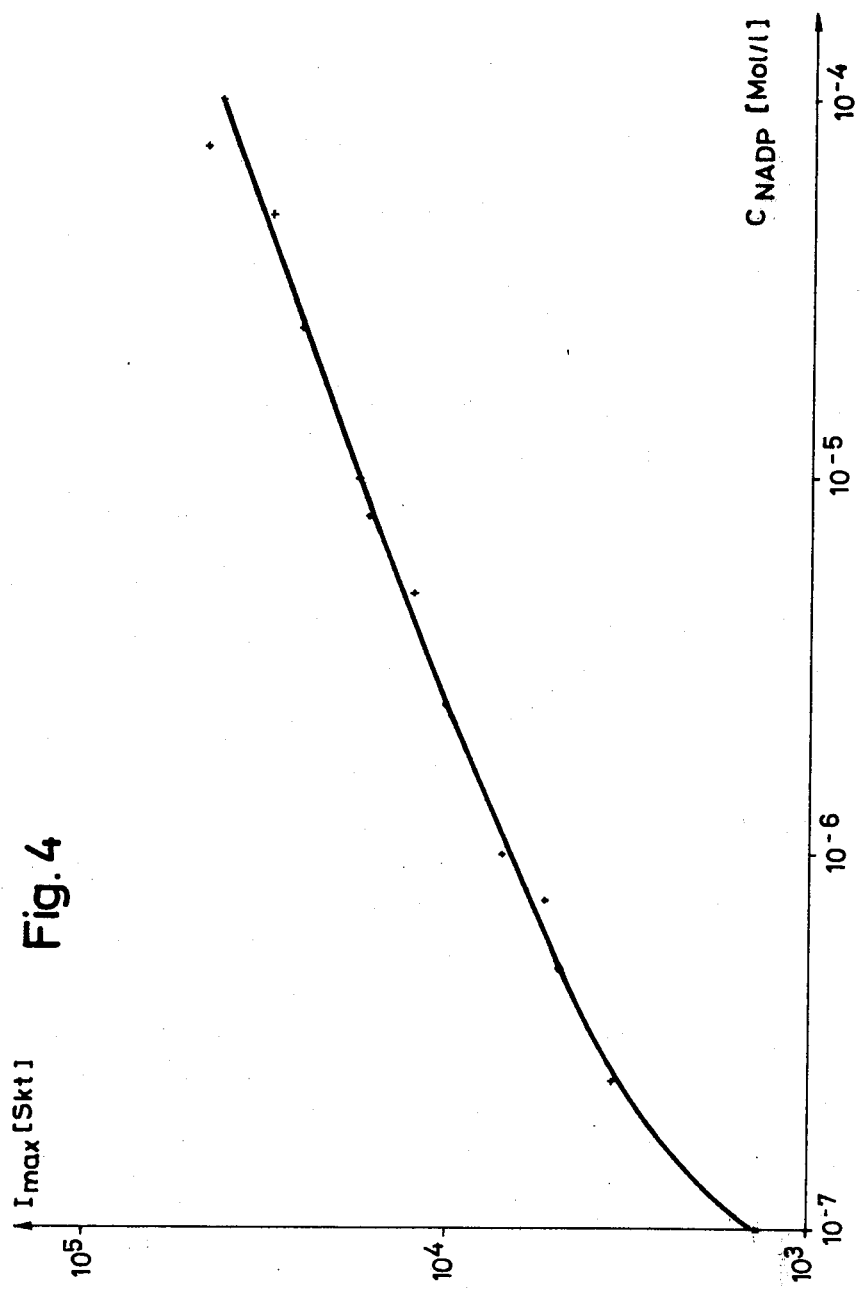
FIG. 4 is a graphic illustration according to FIGS. 1 to 3 for the measurement of the NADP concentration according to Example 4.

FIG. 4 shows the experimental results obtained under these conditions with the use of decanol.

It will be understood that the specification and examples are illustrative, but not limitative of the present invention and that other embodiments within the spirit and scope of the invention will suggest themselves to those skilled in the art.

What is claimed is:

1. Method for the quantitative determination of an oxidized pyridine co-enzyme which comprises reacting a sample containing oxidized pyridine co-enzyme in the presence of its specific alcohol dehydrogenase with an aliphatic alcohol of 8 to 16 carbon atoms, oxidizing the aldehyde formed with reduced flavine mononucleotide and oxygen in the presence of luciferase and of the particular FMN-reductase which is independent of the co-enzyme to be determined and of the reduced substrate co-enzyme of the latter, and measuring the resulting light emission as a measure of the initial oxidized pyrizine co-enzyme content.

2. Method as claimed in claim 1 wherein said luciferase and FMN-reductase is supplied in the form of a crude photobacteria preparation.

3. Method as claimed in claim 1 wherein the oxidized pyridine co-enzyme to be determined is simultaneously formed in a preceding dehydrogenase reaction.

4. Method as claimed in claim 3 wherein there is used purified luciferase and an FMN-reductase preparation which is independent of the oxidized pyridine co-enzyme to be determined and does not contain any FMN-reductase which is independent upon the oxidized pyridine co-enzyme to be determined.

5. Method as claimed in claim 1 wherein NAD is determined.

6. Method as claimed in claim 5 wherein said specific alcohol dehydrogenase is alcohol dehydrogenase from equine liver or yeast.

7. Method as claimed in claim 5 wherein there is used as said specific alcohol dehydrogenase, alcohol dehydrogenase from *Leuconostoc mesenteroides*.

8. Reagent for the determination of an oxidized pyridine co-enzyme comprising
    luciferase;
    FMN reductase;
    an aliphatic alcohol of 8 to 16 carbon atoms;
    a reduced co-enzyme;
    an alcohol dehydrogenase specific for the co-enzyme to be determined;
    flavine-mononucleotide (FMN); and
    a buffer.

9. Reagent as claimed in claim 8 also containing an organic sulphhydryl compound.

10. Reagent as claimed in claim 8 also containing a surface-active agent.

11. Reagent as claimed in claim 8 comprising
    0.5 to 50 µg/ml luciferase/FMN-reductase preparation;
    0.5 to 300 mU/ml alcohol dehydrogenase;
    0.01 to 25 mMol/l aliphatic alcohol of 8 to 16 carbon atoms;
    2 to 130 mMol/l buffer, pH 6 to 9;
    1 to $250 \times 10^{-6}$ Mol/l reduced co-enzyme;
    and, optionally,
    0.002 to 0.5 mMol/l organic sulphhydryl compound.

12. Reagent as claimed in claim 8 comrising
    1.8 to 40 µg/ml luciferase/FMN-reductase preparation;
    1.3 to 2.7 mU/ml alcohol dehydrogenase;
    0.1 to 10 mMol/l alcohol;
    5 to 50 mMol/l buffer;
    5 to $150 \times 10^{-6}$ Mol/l reduced pyridine co-enzyme;
    and, optionally,
    0.005 to 0.5 mMol/l organic sulphyhydryl compound.

13. Reagent as claimed in claim 8 wherein the sulphyhydryl compound is mercaptoethanol.

14. Reagent as claimed in claim 8 wherein said reagent contains an aralkyl-polyoxyethylene ester or ether as a surface-active agent.

* * * * *